United States Patent [19]

Kono et al.

[11] Patent Number: 5,314,810
[45] Date of Patent: May 24, 1994

[54] FRUCTOSE TRANSFERRING ENZYME ABSORBED ON A GRANULAR CARRIER FOR PRODUCTION OF FRUCTOOLIGOSACCHARIDES

[75] Inventors: Toshiaki Kono; Goichi Yamaguchi; Hidemasa Hidaka, all of Kanagawa, Japan

[73] Assignee: Meiji Seika Kaisha, Ltd., Tokyo, Japan

[21] Appl. No.: 885,001

[22] Filed: May 19, 1992

Related U.S. Application Data

[63] Continuation of Ser. No. 766,970, Sep. 26, 1991, abandoned, which is a continuation of Ser. No. 275,496, Nov. 23, 1988, abandoned.

[30] Foreign Application Priority Data

Nov. 25, 1987 [JP] Japan .................. 62-295299

[51] Int. Cl.$^5$ ............... C12P 19/18; C12N 11/10; C12N 11/08
[52] U.S. Cl. ..................... 435/97; 435/101; 435/178; 435/180; 435/181
[58] Field of Search ............... 435/97, 101, 178, 180, 435/181

[56] References Cited

U.S. PATENT DOCUMENTS 4,239,854  12/1980  Hirohara et al. .......... 435/180 X
4,390,626   6/1983  Chibata et al. .......... 435/181 X

FOREIGN PATENT DOCUMENTS 0162292   9/1983  Japan ................. 435/97
62-40289   2/1987  Japan .
2072679  10/1981  United Kingdom .

Primary Examiner—David M. Naff
Attorney, Agent, or Firm—Sughrue, Mion, Zinn, Macpeak & Seas

[57] ABSTRACT

A fructose transferring enzyme is immobilized by adsorption on a granular carrier having a primary to quaternary amine. The carrier is preferably an epoxy polymer, a vinyl polymer or a chitosan derivative having a primary, secondary or tertiary amine. Immobilization can be performed without or with a crosslinking agent. The immobilized enzyme is used for producing fructooligosaccharides by passing a sucrose solution through a column containing the immobilized enzyme.

21 Claims, No Drawings

FRUCTOSE TRANSFERRING ENZYME ABSORBED ON A GRANULAR CARRIER FOR PRODUCTION OF FRUCTOOLIGOSACCHARIDES

This is a continuation of application Ser. No. 07/766,970 filed Sep. 26, 1991, which in turn is a continuation of application Ser. No. 07/275,496 filed Nov. 23, 1988, both now abandoned.

FIELD OF THE INVENTION

The present invention relates to an immobilized enzyme suitable for use in the production of fructooligosaccharides which are used in food and other industries as low-cariogenic sweeteners, low calorie sweeteners, sweeteners having a lipid metabolism improving action and a selective proliferating promoting action on intestinal bifidobacteria and so on, a process for production of such immobilized enzyme, and a process for production of fructooligosaccharides with the use of said immobilized enzyme.

BACKGROUND OF THE INVENTION

It is known that when sucrose is contacted with an enzyme having fructose transferring activity (hereinafter referred to generally as fructose transferring enzyme), there is obtained a sweetener containing products of fructose transfer reaction, such as glucose as a byproduct, fructooligosaccharides which are mostly the trisaccharide ($GF_2$), tetrasaccharide ($GF_3$), pentasaccharide ($GF_4$) and hexasaccharide ($GF_5$) corresponding to sucrose coupled with 1 to 4 moles of fructose, respectively, and as a minor component, unreacted sucrose. It is further known that these fructooligosaccharides are not-substrates for the dextran sucrase produced by *Streptococcus mutans*, the cariogenic bacterium, and that a low-cariogenic sweetener can be produced by permitting a fructose enzyme to act on sucrose (JP-A-56-154967; the term "JP-A" used herein means "an unexamined published Japanese patent application"). It is also known that fructooligosaccharides are low-calorie sweeteners which are not digested in the living body (JP-A-58-40065) and are selectively utilized by bifidobacteria forming main part of the inetestinal bacterial flora, they can be accordingly used as selective growth factors for intestinal bifidobacteria (JP-B-59-53834; the term "JP-B" used herein means "an examined published Japanese patent application").

As the fructose transferring enzyme which can be used in the production of fructooligosaccharides, there can be mentioned the enzymes derived from strains of the genus Aspergillus such as *A. niger* etc., those of the genus Penicillium such as *P. nigricans* etc., those of the genus Fusarium such as *F. lini* IAM 5008 etc., those of the genus Gloeosporium such as *G. kaki* IAM 5011 etc., and those of the genus Aureobasidium such as *A. pullulans* var. *melanigenum* A-8 ATCC 20612 and so on. Aside from the above-mentioned microorganisms, the enzymes derived from yeasts and other microorganisms, for example strains of the genus Saccharomyces such as *S. cerevisiae* etc., those of the genus Rhodotorula such as *R. glutinis* etc., those of the genus Pichia such as *P. miso* etc., those of the genus Hansenula such as *H. miso* etc., and those of the genus Candida such as *C. tropicalis* etc., as well as the enzymes derived from certain plants such as asparagus, Jerusalem artichoke and so on (JP-A-56-154967 and JP-B-59-53834) can be utilized.

As an industrial process for production of fructooligosaccharides using a native fructose transferring enzyme, there is known a batch process in which a culture broth of such microorganism or the cells, disrupted cells, extract or enzyme harvested or purified therefrom is stirred together with sucrose at suitable sucrose concentration, pH and temperature (JP-A-56-154967 and 61-268190).

From the standpoint of production cost, a continuous process using an immobilized enzyme or an immobilized microorganism is preferred to a batch process with native enzyme and for this purpose, it has been proposed to immobilize microbial cells with an alginate gel by entrapping immobilization (JP-A-58-162292) or with $\beta$-1,3-1,6-glucan and aluminum sulfate (JP-A-60-41497).

In order to produce fructooligosaccharides using an immobilized enzyme or an immobilized microorganism continuously on an industrial scale, it is necessary to pack the immobilized enzyme or the like into a column and pass a highly concentrated sucrose solution through the column. However, in order that this process may be successfully carried out, the immobilized enzyme or the like must have a fairly high mechanical strength. Generally speaking, an immobilized enzyme or the like obtained by gel entrapment is comparatively low in mechanical strength so that in industrial production using a highly concentrated sucrose solution as the substrate, the gel tends to be compacted to cause a progressive decrease in flow rate.

To obviate this disadvantage, entrapping immobilized microbial cells (JP-A-62-40289) and entrapping immobilized enzymes (JP-A-62-278983), having improved mechanical strength characteristics have been developed.

However, when such an immobilized preparation is packed into a column and a substrate solution is passed under industrial conditions, for example at a temperature of 50° C. and a sucrose concentration of 50%, there are encountered difficulties such that the half-life of the enzyme activity is as short as about 20 days, the output and composition of the desired product vary considerably, and the withdrawal and repacking of the immobilized cells or enzyme must be carried out frequently.

SUMMARY OF THE INVENTION

The intensive research undertaken by the present inventors to overcome the above-mentioned disadvantages led to the finding that with an immobilized enzyme obtainable by causing a granular carrier, such as beads of a chitosan derivative or anion exchange resin having primary to quaternary amines, to adsorb a predetermined amount of fructose transferring enzyme, not only are fructooligosaccharides produced in high yield but the half-life of the enzyme activity is remarkably prolonged. The present invention has been accomplished on the basis of the above finding.

The present invention relates to an immobilized enzyme comprising a fructose transferring enzyme immobilized on a granular carrier having primary to quaternary amines, a process for producing an immobilized enzyme which comprises contacting a solution of fructose transferring enzyme with a granular carrier having primary to quaternary amines, and a process for producing fructooligosaccharides which comprises contacting sucrose with an immobilized enzyme consisting in a fructose transferring enzyme immobilized on a granular carrier having primary to quaternary amines.

The process for immobilization of fructose transferring enzyme according to the present invention is as simple as mixing a solution of the enzyme with a carrier under stirring and, as such, is by far more expedient and economical than any known process. Furthermore, the yield of fructooligosaccharide obtainable with this immobilized enzyme is comparable to the yield obtainable by a batch process employing native enzyme and the yield and composition of the reaction product can be well controlled in a wide range. Moreover, since the mere passage of the substrate solution through the immobilized enzyme column involves only a short reaction time, the decolorization and desalting procedure necessary for a downstream product can be considerably simplified. In this sense, too, the present invention has a remarkable merit on the industrial production. The most important advantage of the present invention over the conventional immobilization processes is that the half-time of the immobilized enzyme activity can be twice or more as long. This means that fructooligosaccharide can be produced on an industrial scale with considerable advantage. Thus, compared with the batch process using a native enzyme, the productivity per unit amount of used enzyme is at least 20 times as high. Furthermore, the carrier of the immobilized enzyme can be reclaimed, for example by treatment with a dilute alkali solution, for reuse. This is another major advantage of the present invention.

DETAILED DESCRIPTION OF THE INVENTION

The fructose transferring enzyme used in the present invention may be obtained from a culture broth of such a microorganism as mentioned above in which the desired enzyme has been induced or secreted, which is obtainable by growing said microorganism in an appropriate culture medium, for example a medium composed of 5.0% of sucrose, 1.0% of peptone, 0.7% of meat extract and 0.3% of sodium chloride, at the optimal temperature for growth of the particular strain of microorganism, for example 25° to 30° C., for a period ranging from about 24 to 96 hours.

When the fructose transferring enzyme is secreted as an extracellular enzyme, the enzyme solution can be prepared from the culture broth by centrifugation or filtration. When the enzyme is intracellularly produced, it can be prepared from the microbial cells by known techniques such as sonication, and mechanical disruption. The high pressure crude enzyme thus obtained may be further purified by one or more of the following methods such as ultrafiltration, ammonium sulfate fractionation, precipitation with an organic solvent, gel filtration chromatography, ion exchange chromatography or the like.

As the fructose transferring enzyme producing strain, *Aspergillus niger* ATCC 20611 and *Aureobasidium pullulans* var. *melanigenum* A-8 ATCC 20612 (both deposited under the Budapest treaty) are preferably used.

The carrier to be used for immobilizing the enzyme in accordance with the present invention may for example be beads of a chitosan derivative, anion exchange resin or the like which carries primary to quaternary amines as the functional groups essential to immobilization. Cation exchange resins, adsorbent resins, activated carbon, etc. are not suitable for the purposes of the present invention. The preferred matrices for the carrier are polysaccharides such as chitosan or styrene-divinylbenzene, epoxy, vinyl and phenolic polymers. Chitosan derivatives, polystyrene, epoxy and polyvinyl are particularly preferred. Acrylic polymers are not suitable.

Specific examples of amines used as the functional groups include a primary or secondary amine, e.g., $-NH_2$, $-NHR$,

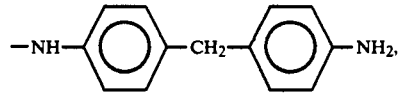

$-CH_2NH(CH_2)_nNH_2$; a tertiary amine, e.g., $-NR_2$, $-CH_2-N(CH_3)_2$, $-(CH_2)_n-N-(CH_2CH_3)_2$; and a quaternary amine, e.g., $-N^+R_3$ $-CH_2^+N(CH_3)_3$, $-CH_2^+N(CH_3)_2CH_2CH_2OH$, $-CH_2^+N(CH_3)_2(CH_2)_n-^+N(CH_3)CH_2R$.

Examples of commercially available carriers include Diaion ® (the trademark of Mitsubishi Kasei Corporation) WA-21, WA-30, and HPA-25; Sepabeads ® (the trademark of Mitsubishi Kasei Corporation) FP-HA and FP-DA; Toyopearl ® (the trademark of Tosoh Corporation) DEAE-Toyopearl; Doulite ® (the trademark of Diamond Sharmrock) A-365, A-7, A-368, A-378, A-161 and A-561; Dowex ® (the trademark of Dow Chemical Co.) 66, MSA-1 and WGR-2; Amberlite ® (the trademark of Japan Organo Co., Ltd.) IRA-45, IRA-93, IRA-94, IRA-99, IRA-401, IRA-411 and IRA-904; Chitopearl ® (the trademark of Fujibo Inc.) BCW-2500, BCW-2600, BCW-3000, BCW-3500 and BCW-4000. Among these, carriers having primary to tertiary amine such as Diaion WA-21 and WA-30; Sepabeads FP-DA and FP-HA; DEAE-Toyopearl, Duolite A-365, A-7, A-368 and A-378; Dowex 66 and WGR-2; Amberlite IRA-45, IRA-93, IRA-94 and IRA-99; Chitopearl BCW -2600, BCW-3000, BCW-3500, and BCW-4000 are particularly preferred.

The process for producing the immobilized enzyme according to the invention is described below.

While the amount of the enzyme relative to the carrier may vary over a broad range, the preferred proportion is 25 to 5,000 units of the enzyme per gram of the carrier and preferably 50 to 3,000 units/gram. The method for assay of fructose transferring activity and the indication of enzyme activity are as follows.

One milliliter of a sample enzyme solution is mixed with 2.0 ml of McIlvaine buffer (pH 5.0) or, in the case of an immobilized enzyme, an appropriate amount of the immobilized enzyme is added to 3 ml of the same buffer. Then, 2.0 ml of a 25% (w/v) solution of sucrose is added and the mixture is incubated at 40° C. for 1 hour. To stop the reaction, the reaction mixture is hold in boiling water for 10 minutes. The $GF_2$ produced in the reaction mixture is assayed by high performance liquid chromatography. One unit of activity is defined as the amount of enzyme which produce 1 micromole of $GF_2$ per minute in the reaction mixture.

When the amount of the enzyme is over 5000 units/g carrier, the rate of enzyme immobilization is too low and the yield of fructooligosaccharide is also adversely affected. Conversely when the amount of the enzyme is less than 25 units/g carrier, the immobilized enzyme is virtually useless from economic points of view.

The immobilization pH is dependent on the stability of the enzyme and the adsorptive affinity of the enzyme to the carrier. Generally speaking, the enzyme dissolved in aqueous medium at pH 3 to 10, preferably pH 4 to 9, is mixed with the carrier and stirred. Stirring may be effected manually or mechanically. The stirring time required depends on the amounts of the materials, temperature, pH, etc. Generally an immobilized enzyme can be obtained after 0.5 to 5 hours of stirring. While a wet carrier is conducive to a reduction in immobilization time, a dry carrier may also be employed.

The immobilization temperature is 0° to 50° C. where the enzyme may be stable. The immobilization procedure may be immediately followed by rinsing with water at 0° to 50° C. for removal of impurities. After the above immobilization procedure, the enzyme may be further securely immobilized by means of a water-soluble polyfunctional crosslinking agent such as glutaraldehyde. If the immobilized enzyme is to be dried, it can be dried either in vacuo or in a current of air at a temperature not exceeding 60° C.

The process for production of fructooligosaccharide using the above immobilized enzyme is described below. As the most practical method, the immobilized enzyme is packed into a column and sucrose solution is passed through the column. A batch process or a fluidized bed process can also be available. For the column system production of fructooligosaccharide, preferably a sucrose solution of 20 to 70% (w/w) concentration is passed through the column at pH 5-8 and temperature of 30° to 60° C. The yield and composition of fructooligosaccharide obtainable under such conditions can be controlled by adjusting the activity and amount of the immobilized enzyme and the flow rate of the substrate sucrose solution. Thus, fructooligosaccharide may be obtained in a maximum yield of about 62 percent (w/w dry basis).

The thus-obtained fructooligosaccharide may be purified by treating with carbon black or ion exchange resin.

The carrier of the immobilized enzyme whose activity has been consumed can be reclaimed by the known procedure of removing the enzyme protein with a dilute alkali solution and can be used repeatedly for immobilization.

The following examples are further illustrative of the present invention, but are not to be construed to limit the scope thereof.

EXAMPLE 1 AND COMPARATIVE EXAMPLE (1) Preparation of the Enzyme

*Aspergillus niger* ATCC 20611 was inoculated into a medium (300 ml) containing 2% of bouillon and 5% of sucrose and incubated at 28° C. for 24 hours to prepare a seed culture. A jar fermenter of 30-liter capacity was charged with 15 l of a medium containing 15% of sucrose and 3.6% of yeast extract and sterilized at 120° C. for 30 minutes. A 10 ml portion of the above seed culture was then transferred to the jar fermenter and incubated at 28° C. for 96 hours under submerged aerobic culture conditions of 400 rpm and 1.0 vvm. After completion of incubation, the resulting culture broth was filtered to remove the mycelium and recover a filtrate with fructose transferase activity. This filtrate was purified using an ultrafiltration membrane equipment (cut-off molecular weight: 10,000) and concentrated to give an enzyme solution. The enzymatic activity of this solution was 2,500 U/ml.

(2) Preparation of the Immobilized Enzyme

Using the 14 different commercial carriers indicated in Table 1, the enzyme solution prepared in (1) above was caused to be adsorbed on each carrier at a rate of 700 U/g carrier and under the immobilization conditions of pH 5-8 and room temperature with constant stirring. The resulting immobilized enzyme was rinsed with deionized water and its activity was determined. Thus, the enzymatic activity of the non-adsorbed solution was measured and the difference between this activity and the initial activity of the enzyme used was divided by the initial activity to arrive at the immobilization rate (%). The activity of the immobilized enzyme was also assayed and taken as the apparent activity.

Using the immobilized enzymes which were found to have enzymatic activity, their fructooligosaccharide production performances were tested. Thus, under the conditions of 60% (w/w) sucrose concentration, pH 6.0 and 60° C., the amount of each immobilized enzyme equivalent to 2.5 units (apparent activity) per gram sucrose was subjected to reaction for 20 hours and the yield of fructooligosaccharide (on a solid/solid basis) was determined by high performance liquid chromatography.

Each of the immobilized enzymes giving sufficient yields of fructooligosaccharide was packed into a column and the trial column system reaction was carried out. Thus, the immobilized enzyme was packed into a column measuring 22 mm in inside diameter to a packing height of 10 cm (38 ml) and a 50% (w/w) sucrose solution was passed at a flow rate conducive to the maximal yield of fructooligosaccharide under the conditions of pH 6.0 and 50° C. The column effluent was analyzed by high performance column chromatography. The enzymatic activities were determined at timed intervals to find half-life of the enzyme activities. The results are shown in Table 1.

TABLE 1

| Test No. | Carrier | | | | Immobilized enzyme | | | |
|---|---|---|---|---|---|---|---|---|
| | | | | | Apparent** activity | Yield of fructooligosaccharide (%) | | Activity half-life |
| | Sample | Matrix | Type | Functional Group | (units/g) | Batch | Column | (days) |
| 1* | Diaion HPK-25 | Copolymer styrene-divinylbenzene | Strong acid | Sulfonate | — | — | — | — |
| 2* | Duolite S-861 | Copolymer styrene-divinylbenzene | Adsorbent | None | — | — | — | — |
| 3 | Diaion WA-21 | Copolymer styrene-divinylbenzene | Weak base | Primary/secondary amine | + | 52 | 56 | 50 |
| 4 | Diaion WA-30 | Copolymer styrene-divinylbenzene | " | Tertiary amine | ++ | 53 | 57 | 60 |
| 5 | Duolite A-161 | Copolymer styrene-divinylbenzene | Strong base | Quaternary amine (type I) | + | 56 | 58 | 42 |
| 6 | Dowex MSA-2 | Copolymer styrene-divinylbenzene | " | Quaternary amine (type II) | ++ | 56 | 60 | 39 |

TABLE 1-continued

| Test No. | Carrier | | | | Immobilized enzyme | | | Activity half-life (days) |
|---|---|---|---|---|---|---|---|---|
| | Sample | Matrix | Type | Functional Group | Apparent** activity (units/g) | Yield of fructo-oligosaccharide (%) | | |
| | | | | | | Batch | Column | |
| 7 | Dowex WGR-2 | Epoxy resin | Weak base | Primary-quaternary amine | +++ | 60 | 60 | 50 |
| 8 | Duolite A-561 | Phenolic resin | " | Tertiary amine | ++ | 53 | 57 | 45 |
| 9* | Diaion WK-20 | Polyacrylic acid | Weak acid | Carboxylic acid | + | 2 | — | — |
| 10* | Amberlite IRA-35 | " | Weak base | Tertiary amine | + | 2 | — | — |
| 11* | Sepabeads FP-CM | Vinyl polymer | Weak acid | Carboxylic acid | — | — | — | — |
| 12 | Sepabeads FP-HA | " | Weak base | Primary amine | ++ | 55 | 57 | 53 |
| 13 | Chitopearl BCW-3000 | Chitosan derivative | " | Primary/secondary amine | ++ | 57 | 59 | 65 |
| 14 | Chitopearl BCW-2500 | Chitosan derivative | Strong base | Quaternary amine | +++ | 59 | 60 | 42 |

*Comparative examples
**—: no activity,
+: 1–100 U/g,
++: 101–200 U/g,
+++: ≧201 U/g.

EXAMPLE 2

*Aureobasidium pullulans* var. *melanigenum* A-8 (ATCC 20612) was inoculated into 40 ml of a medium containing 2% of bouillon and 5% of sucrose in an Erlenmeyer flask and cultured at 28° C. for 24 hours to prepare a seed culture. A jar fermenter of 3-liter capacity was charged with 1.5 l of a medium containing 15% of sucrose, 1% of peptone, 0.7% of meat extract, 0.3% of NaCl and 0.1% of $CoCl_2 \cdot 6H_2O$ and sterilized at 120° C. for 30 minutes. Then, 40 ml of the above seed culture was transfered to this jar fermenter and submerged aerobic culture was carried out at 28° C., 240 rpm and 1.0 vvm for 24 hours. After completion of incubation, the resulting broth was centrifuged to recover 30 g of cells containing the desired fructose transferring enzyme.

The above cells were disrupted by sonication and centrifuged. The supernatant was subjected to fractional precipitation with ammonium sulfate and dialysis to give 50 ml of a crude enzyme solution (activity 120 U/ml).

The enzyme solution was then contacted with Amberlite IRA-94 (a weak base anion exchange resin, matrix: Copolymer styrene-divinylbenzene, functional group: tertiary amine; Japan Organo Co., Ltd. (50 g) at pH 4.2 and room temperature for 30 minutes, with constant stirring. After adsorption, the reaction system was subjected to solid-liquid separation and the enzymatic activity was assayed. As a result, the immobilization rate was nearly 100% and the apparent activity was 95 U/g. This immobilized enzyme was packed into a column measuring 2.2 cm in inside diameter and a 70% solution of sucrose was passed through the column at pH 7.0 and 60° C. At a space velocity of 0.5 per hour, the yield of fructooligosaccharide was maximal, being about 54% on a solid/solid basis. The half-life at 50° C. was 67 days.

EXAMPLE 3

A loopful of *Aspergillus niger* ATCC 20611 was inoculated into a medium (10 ml) containing 2% of bouillon and 5% of sucrose and incubated at 28° C. for 24 hours to give a seed culture. A jar fermenter of 3-liter capacity was charged with 1.5 l of a medium containing 15% of sucrose and 3.6% of yeast extract and sterilized at 120° C. for 30 minutes. Then, 10 ml of the above seed culture was transferred to the jar fermenter and submerged aerobic culture was carried out at 28° C., 240 rpm and 0.5 vvm for 96 hours. After completion of incubation, the culture broth was filtered to give 180 g of mycelium and 1.2 l of filtrate. The enzymatic activity of the filtrate was 100 U/ml. A 50 ml portion of this filtrate was diluted two-fold and contacted with 100 g of Diaion FP-DA (a weakly basic resin, matrix: vinyl polymer; functional group: DEAE tertiary amine; Mitsubishi Kasei Corporation) at pH 8.7 and 45° C. for 5 hours for immobilization of the enzyme. The immobilized enzyme thus obtained was rinsed and its activity was assayed. The immobilization rate was 93% and the apparent activity was 16 U/g. Using this immobilized enzyme, a batch reaction was carried out under the same conditions as Example 1 (except that the temperature was 50° C.). The yield of fructooligosaccharide was 58% on a solid/solid basis. There occurred no loss of activity of the immobilized enzyme.

EXAMPLE 4

The cells separated in Example 2 were subjected to freeze-thaw treatment, sonication and autolysis, followed by extraction and centrifugation to give a crude enzyme solution. This crude enzyme solution was purified by ammonium sulfate fractionation, ion exchange column chromatography, gel filtration, ultrafiltration, dialysis and concentration, whereby a highly purified enzyme (2,000 U/mg protein) was obtained in an amount equivalent to about 29,000 units.

This enzyme was immobilized by contacting it with 10 g of Chitopearl BCW 3500 (a chitosan derivative having primary and secondary aromatic amines; Fujibo Inc.) at pH 5.5 and 3° C. for 5 hours with stirring. After rinsing, the immobilization rate was 63% and the apparent activity was 560 U/g. This immobilized enzyme was packed into a column measuring 1 cm in inside diameter and a 40% solution of sucrose was passed through the column at pH 5.0 and 40° C. for 15 days. As a result, there was found no loss of enzymatic activity. A 40% (w/w) sucrose solution was further passed through the column at 50° C. and the half-life of the enzyme was determined. The half-life was about 80 days.

While the invention has been described in detail and with reference to specific embodiments thereof, it will be apparent to one skilled in the art that various changes and modifications can be made therein without departing from the spirit and scope thereof.

We claim:

1. An immobilized enzyme adsorbed to a granular carrier, said immobilized enzyme being produced by a process consisting essentially of the step of immobilizing free enzyme having fructose transferring activity by adsorbing the free enzyme onto the granular carrier, said immobilizing step being carried out without the use of a crosslinking agent, wherein said carrier is selected from the group consisting of epoxy polymers, vinyl polymers and chitosan derivatives, each containing at least one primary, secondary, or tertiary amine.

2. The immobilized enzyme of claim 1 wherein said enzyme having fructose transferring activity is derived from *Aspergillus niger* ATCC 20611.

3. The immobilized enzyme of claim 1 wherein said enzyme having fructose transferring activity is derived from *Aureobasidium pullulans* var. melanigenum ATCC 20612.

4. The immobilized enzyme of claim 1, wherein the amount of said enzyme having fructose transferring activity relative to said granular carrier is in the range of 50 to 3,000 units of the carrier.

5. The immobilized enzyme of claim 1, wherein the immobilization is carried out at a pH of from 3 to 10 at 0° to 50° C. for 0.5 to 5 hours while stirring.

6. The immobilized enzyme of claim 1, wherein said carrier is a styrene-divinylbenzene copolymer having a tertiary amine.

7. The immobilized enzyme of claim 1, wherein said carrier is a vinyl polymer having a tertiary amine.

8. The immobilized enzyme of claim 1, wherein said carrier is a chitosan derivative having a primary or secondary amine or a secondary amine containing aniline.

9. The immobilized enzyme of claim 1, wherein said vinyl polymer is a styrene-divinylbenzene copolymer.

10. The immobilized enzyme of claim 1, wherein 25 to 5,000 units of enzyme are immobilized per gram of said granular carrier.

11. A process for producing an immobilized enzyme adsorbed to a granular carrier, said process consisting essentially of the step of immobilizing free enzyme having fructose transferring activity by adsorbing the free enzyme onto the granular carrier, said immobilizing step being carried out without the use of a crosslinking agent, wherein said carrier is selected from the group consisting of epoxy polymers, vinyl polymers and chitosan derivatives, each containing at least one primary, secondary or tertiary amine.

12. The process of claim 11 wherein the amount of said enzyme having fructose transferring activity relative to said granular carrier is in the range of 50 to 3,000 units per gram of the carrier.

13. The process of claim 11 wherein the immobilizing step is carried out at pH 3 to 10 at 0° to 50° C. for 0.5 to 5 hours under stirring.

14. The process of claim 11, wherein said carrier is a styrene-divinylbenzene copolymer having a tertiary amine.

15. The process of claim 11, wherein said carrier is a vinyl polymer having a tertiary amine.

16. The process of claim 11, wherein said carrier is a chitosan derivative having a primary or secondary amine or a secondary amine containing aniline.

17. A process for producing a fructooligosaccharide, wherein said process comprises the step of contacting sucrose with an immobilized enzyme having fructose transferring activity, wherein said enzyme is immobilized by adsorbing free enzyme having fructose transferring activity onto a granular carrier, said immobilizing step being carried out without the use of a crosslinking agent, wherein said carrier is selected from the group consisting of epoxy polymers, vinyl polymers and chitosan derivatives, each containing at least one primary, secondary, or tertiary amine.

18. The process of claim 17 wherein said step of contacting sucrose with immobilized enzyme comprises passing a 20 to 70% (w/w) solution of sucrose through a column of said immobilized enzyme at pH 5 to 8 and 30° to 60° C.

19. The process of claim 17, wherein said carrier is a styrene-divinylbenzene copolymer having a tertiary amine.

20. The process of claim 17, wherein said carrier is a vinyl polymer having a tertiary amine.

21. The process of claim 17, wherein said carrier is a chitosan derivative having a primary or secondary amine or a secondary amine containing aniline.

* * * * *